United States Patent
Reever

(10) Patent No.: US 6,790,223 B2
(45) Date of Patent: Sep. 14, 2004

(54) DELIVERING A URETHERAL STENT

(75) Inventor: Kenneth P. Reever, Hopedale, MA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/961,129

(22) Filed: Sep. 21, 2001

(65) Prior Publication Data

US 2003/0060870 A1 Mar. 27, 2003

(51) Int. Cl.$^7$ .................................................. A61F 2/06
(52) U.S. Cl. ....................................... 623/1.12; 606/108
(58) Field of Search ............................. 606/108, 191, 606/192, 194, 195; 623/1.12, 1.11, 1.17, 1.22, 23.7, 23.69, 23.66

(56) References Cited

U.S. PATENT DOCUMENTS

| | | |
|---|---|---|
| 3,527,226 A | 9/1970 | Hakim et al. |
| 3,657,744 A | 4/1972 | Ersek |
| 3,938,529 A | 2/1976 | Gibbons |
| 4,156,067 A | 5/1979 | Gould |
| 4,240,434 A | 12/1980 | Newkirk |
| 4,423,725 A | 1/1984 | Baran et al. |
| 4,660,560 A | 4/1987 | Klein |
| 4,768,507 A | 9/1988 | Fischell et al. |
| 4,771,773 A * | 9/1988 | Kropf .......................... 606/108 |
| 4,895,566 A | 1/1990 | Lee |
| 4,932,938 A | 6/1990 | Goldberg et al. |
| 4,973,301 A | 11/1990 | Nissenkorn |
| 4,990,155 A | 2/1991 | Wilkoff |
| 4,994,066 A | 2/1991 | Voss |
| 5,037,427 A | 8/1991 | Harada et al. |
| 5,041,092 A | 8/1991 | Barwick |
| 5,059,169 A | 10/1991 | Zilber |
| 5,061,275 A | 10/1991 | Wallsten et al. |
| 5,078,720 A | 1/1992 | Burton et al. |
| 5,122,154 A | 6/1992 | Rhodes |

(List continued on next page.)

FOREIGN PATENT DOCUMENTS

| | | |
|---|---|---|
| EP | 0 274 846 | 7/1988 |
| EP | 0 341 988 | 11/1989 |
| WO | WO 80/01460 | 7/1980 |

(List continued on next page.)

OTHER PUBLICATIONS

Patent Cooperation Treaty, International Search Report, International Application No. PCT/US 02/29537, mailed on Mar. 26, 2003, 6 pages.

Primary Examiner—David O. Reip
Assistant Examiner—Jessica R Baxter
(74) Attorney, Agent, or Firm—Testa, Hurwitz & Thibeault, LLP

(57) ABSTRACT

A delivery system for placement of a stent within a body of a patient includes a stent, a retaining structure, and an elongated member. The stent includes a coil which defines a lumen and has an initial length when in an expanded rest state. Adjacent turns of the coil are positioned to substantially prevent tissue ingrowth through the turns and into the lumen when the stent is placed within the body. The retaining structure is sized for insertion into the body and includes one or more pins. The pins collapse and deform the stent while the stent maintains substantially its initial length. The elongated member is coupled to the retaining structure and enables insertion of the retaining structure with the stent into the body such that the stent can be deployed from the retaining structure and placed into the body while maintaining substantially its initial length.

20 Claims, 14 Drawing Sheets

U.S. PATENT DOCUMENTS

| | | |
|---|---|---|
| 5,147,370 A | 9/1992 | McNamara et al. |
| 5,160,341 A | 11/1992 | Brenneman et al. |
| 5,167,614 A | 12/1992 | Tessmann et al. |
| 5,176,625 A | 1/1993 | Brisson |
| 5,176,626 A | 1/1993 | Soehendra |
| 5,183,085 A | 2/1993 | Timmermans |
| 5,195,989 A | 3/1993 | Euteneuer |
| 5,222,971 A | 6/1993 | Willard et al. |
| 5,224,953 A | 7/1993 | Morgentaler |
| 5,234,456 A | 8/1993 | Silvestrini |
| 5,258,020 A | 11/1993 | Froix |
| 5,269,802 A | 12/1993 | Garber |
| 5,282,784 A | 2/1994 | Willard |
| 5,282,823 A | 2/1994 | Schwartz et al. |
| 5,286,254 A | 2/1994 | Shapland et al. |
| 5,292,315 A | 3/1994 | Euteneuer |
| 5,304,121 A | 4/1994 | Sahatjian |
| 5,316,016 A | 5/1994 | Adams et al. |
| 5,322,501 A | 6/1994 | Mahmud-Durrani |
| 5,342,348 A | 8/1994 | Kaplan |
| 5,344,395 A | 9/1994 | Whalen et al. |
| 5,356,423 A | 10/1994 | Tihon et al. |
| 5,419,760 A | 5/1995 | Narciso, Jr. |
| 5,421,955 A | 6/1995 | Lau et al. |
| 5,429,634 A | 7/1995 | Narciso, Jr. |
| 5,441,515 A | 8/1995 | Khosravi et al. |
| 5,441,516 A | 8/1995 | Wang et al. |
| 5,464,650 A | 11/1995 | Berg et al. |
| 5,496,277 A | 3/1996 | Termin et al. |
| 5,499,994 A | 3/1996 | Tihon et al. |
| 5,514,176 A | 5/1996 | Bosley, Jr. |
| 5,514,669 A | 5/1996 | Selman |
| 5,536,242 A | 7/1996 | Willard et al. |
| 5,545,208 A | 8/1996 | Wolff et al. |
| 5,549,559 A | 8/1996 | Eshel |
| 5,554,181 A | 9/1996 | Das |
| 5,556,413 A | 9/1996 | Lam |
| 5,562,622 A | 10/1996 | Tihon |
| 5,584,872 A | 12/1996 | LaFontaine et al. |
| 5,588,965 A | 12/1996 | Burton et al. |
| 5,593,403 A | 1/1997 | Buscemi |
| 5,599,306 A | 2/1997 | Klein et al. |
| 5,601,591 A | 2/1997 | Edwards et al. |
| 5,609,629 A | 3/1997 | Fearnot et al. |
| 5,618,299 A | 4/1997 | Khosravi et al. |
| 5,626,562 A | 5/1997 | Castro |
| 5,667,486 A | 9/1997 | Mikulich et al. |
| 5,667,490 A | 9/1997 | Keith et al. |
| 5,676,693 A | 10/1997 | LaFontaine |
| 5,702,361 A | 12/1997 | Evans et al. |
| 5,702,419 A | 12/1997 | Berry et al. |
| 5,723,003 A | 3/1998 | Winston et al. |
| 5,725,549 A | 3/1998 | Lam |
| 5,733,303 A | 3/1998 | Israel et al. |
| 5,738,654 A | 4/1998 | Tihon |
| 5,766,209 A | 6/1998 | Devonec |
| 5,766,238 A | 6/1998 | Lau et al. |
| 5,772,668 A | 6/1998 | Summers et al. .......... 606/108 |
| 5,776,142 A | 7/1998 | Gunderson |
| 5,782,838 A | 7/1998 | Beyar et al. |
| 5,797,952 A | 8/1998 | Klein |
| 5,824,037 A | 10/1998 | Fogarty et al. |
| 5,824,038 A * | 10/1998 | Wall .......... 623/1.12 |
| 5,830,179 A | 11/1998 | Mikus et al. |
| 5,833,707 A | 11/1998 | McIntyre et al. |
| 5,843,103 A | 12/1998 | Wulfman |
| 5,876,445 A | 3/1999 | Andersen et al. |
| 5,888,201 A | 3/1999 | Stinson et al. |
| 5,902,328 A | 5/1999 | LaFontaine et al. |
| 5,911,752 A | 6/1999 | Dustrude et al. |
| 5,916,227 A | 6/1999 | Keith et al. |
| 5,928,217 A | 7/1999 | Mikus et al. |
| 5,938,670 A | 8/1999 | Keith et al. |
| 5,957,929 A | 9/1999 | Brenneman |
| 5,964,732 A | 10/1999 | Willard |
| 5,964,744 A | 10/1999 | Balbierz et al. |
| 5,976,165 A | 11/1999 | Ball |
| 5,980,550 A | 11/1999 | Eder et al. |
| 6,001,117 A | 12/1999 | Huxel et al. |
| 6,004,328 A | 12/1999 | Solar |
| 6,017,977 A | 1/2000 | Evans et al. |
| 6,019,779 A * | 2/2000 | Thorud et al. .......... 623/1.12 |
| 6,023,638 A | 2/2000 | Swanson |
| 6,024,763 A | 2/2000 | Lenker et al. |
| 6,033,413 A | 3/2000 | Mikus et al. |
| 6,042,606 A | 3/2000 | Frantzen |
| 6,047,218 A | 4/2000 | Whayne et al. |
| 6,050,949 A | 4/2000 | White et al. |
| 6,066,167 A | 5/2000 | Lau et al. |
| 6,066,168 A | 5/2000 | Lau et al. |
| 6,090,103 A | 7/2000 | Hakky et al. |
| 6,090,115 A | 7/2000 | Beyar et al. |
| 6,113,594 A | 9/2000 | Savage |
| 6,113,597 A | 9/2000 | Eggers et al. |
| 6,119,697 A | 9/2000 | Engel et al. |
| 6,126,667 A | 10/2000 | Barry et al. |
| 6,132,460 A | 10/2000 | Thompson |
| 6,132,461 A | 10/2000 | Thompson |
| 6,139,536 A | 10/2000 | Mikus et al. |
| 6,146,416 A | 11/2000 | Andersen et al. |
| 6,152,919 A | 11/2000 | Hakky |
| 6,156,064 A | 12/2000 | Chouinard |
| 6,162,215 A | 12/2000 | Feng |
| 6,162,231 A | 12/2000 | Mikus et al. |
| 6,165,210 A | 12/2000 | Lau et al. |
| 6,174,305 B1 | 1/2001 | Mikus et al. |
| 6,176,875 B1 | 1/2001 | Lenker et al. |
| 6,179,868 B1 | 1/2001 | Burpee et al. |
| 6,187,015 B1 | 2/2001 | Brenneman |
| 6,214,037 B1 | 4/2001 | Mitchell et al. |
| 6,221,081 B1 | 4/2001 | Mikus et al. |
| 6,238,430 B1 | 5/2001 | Klumb et al. |
| 6,254,628 B1 * | 7/2001 | Wallace et al. .......... 623/1.12 |
| 6,334,866 B1 * | 1/2002 | Wall .......... 623/1.12 |
| 6,355,061 B1 * | 3/2002 | Quiachon et al. .......... 623/1.12 |
| 6,371,979 B1 * | 4/2002 | Beyar et al. .......... 623/1.12 |
| 2002/0107540 A1 | 8/2002 | Whalen et al. |

FOREIGN PATENT DOCUMENTS

| | | |
|---|---|---|
| WO | WO 89/03232 | 4/1989 |
| WO | WO 91/16005 | 10/1991 |
| WO | WO 96/23449 | 8/1996 |
| WO | WO 00/15130 | 3/2000 |
| WO | WO 00/16005 | 3/2000 |
| WO | WO 00/18907 | 4/2000 |
| WO | WO 00/19926 | 4/2000 |
| WO | WO 00/21462 | 4/2000 |
| WO | WO 00/51521 | 9/2000 |
| WO | WO 00/56247 | 9/2000 |
| WO | WO 00/59558 | 10/2000 |
| WO | WO 00/69367 | 11/2000 |
| WO | WO 00/69498 | 11/2000 |
| WO | WO 00/76425 | 12/2000 |
| WO | WO 01/10345 A1 | 2/2001 |
| WO | WO 02/05841 A2 | 8/2002 |

\* cited by examiner

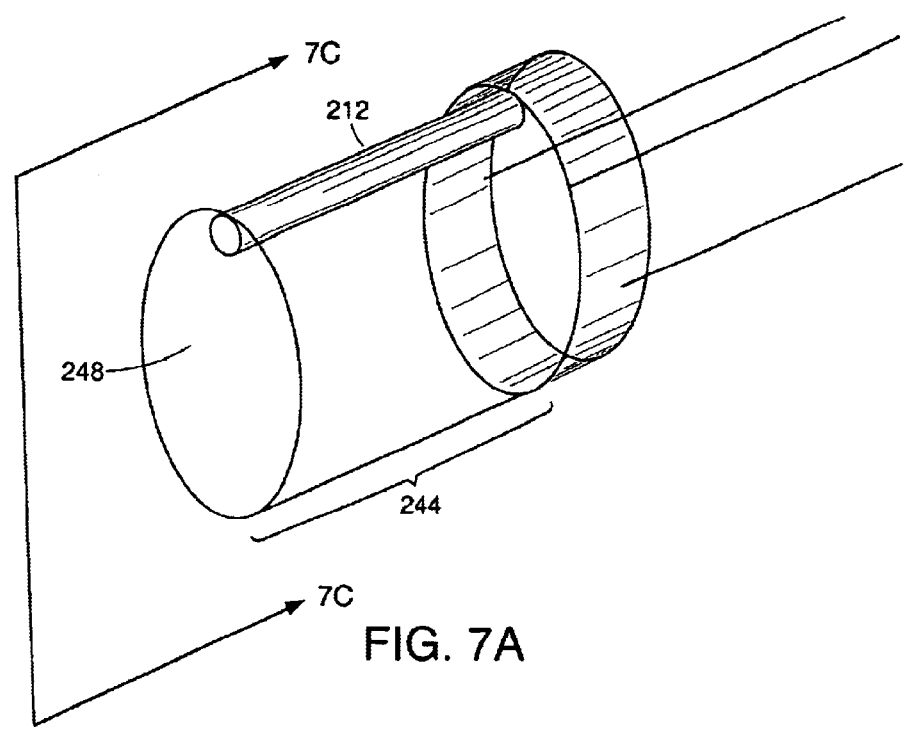
FIG. 7A
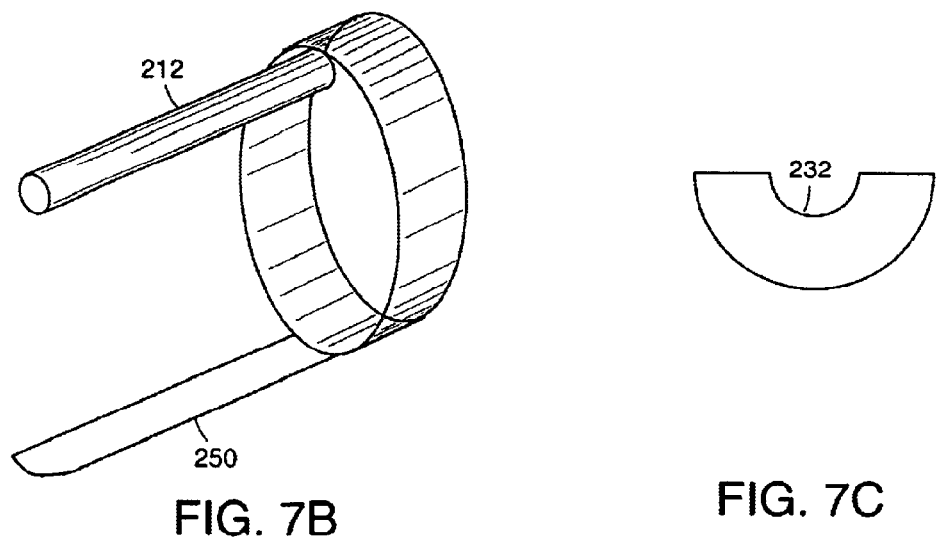
FIG. 7B
FIG. 7C

DELIVERING A URETHERAL STENT

TECHNICAL FIELD

This invention generally relates to stents and delivery systems for inserting stents into the body of a patient.

BACKGROUND INFORMATION

The male urethra is generally a tubular passageway extending from the bladder to the end of the penis. As urine travels from the bladder and out of the body, the urine passes through four sections of the urethra, referred to as the prostatic urethra, the membranous urethra, the bulbar urethra, and the pendulous or distal urethra. Surrounding the prostatic urethra and below the bladder is a prostate gland, which, among other functions, produces the fluid in semen.

A urological condition that some, mostly male, patients experience is blockage of the urethra. For instance, prostate enlargement, also known as benign prostate hyperplasia (BPH), is a common affliction experienced by some men. The condition involves swelling of the prostate, which prevents passage of urine from the bladder and consequently makes urination difficult or impossible. Prostate cancer is another affliction suffered by some men and may lead to many of the same symptoms as BPH.

Medical devices, such as urethral stents, have been developed to correct the problems of urine flow. Urethral stents are designed to hold open one or more of the sections of the urethra obstructing the flow of urine. Generally, these stents are made from a relatively small diameter tube or coil of a biocompatible material such as plastic.

A delivery system is often employed to deliver a urethral stent into the body of the patient. To deliver a urethral coil stent into the body, an existing delivery system typically winds or tightens the coil stent onto the exterior of a delivering catheter to reduce the diameter of the coil stent. The length of the wound stent is greater than the length of the stent in its expanded rest state. That is, prior to winding the coil stent onto the catheter for delivery into the body, and after release of the coil stent in (or outside of) the body, the length of the coil stent is less than when it is wound down onto the exterior of the delivery catheter. The winding thus both reduces the diameter of and extends the length of the coil stent.

SUMMARY OF THE INVENTION

The reduction of length that occurs upon deployment of a urethral coil stent makes it difficult to position accurately the coil stent within the urethra. The invention involves allowing a physician or other medical practitioner or professional to deploy and position a coil stent in a patient's urethra without any substantial change in the length of the coil stent. Urethral coil stent delivery systems and related methods according to the invention allow accurate placement of the stent.

To avoid damaging surrounding structures (such as the external sphincter), a medical professional typically employs a scope (e.g., endoscope) to view the location at which the urethral coil stent will be placed. The medical professional can use the scope to line up the proximal end of the coil stent with the neck of the bladder. The length reduction that typically occurs when deploying a known urethral coil stent, however, frustrates the professional's ability to place accurately the stent even when a scope is used.

In one aspect, the invention generally relates to a delivery system for placement of a stent within the body of a patient. The stent includes a coil, an elongated member, and a retaining structure. The coil defines a lumen and has an initial length when the stent is resting in an expanded equilibrium, or rest, state. Additionally, adjacent turns of the coil are positioned to substantially prevent tissue ingrowth through the turns and into the lumen when the stent is placed within the body. The retaining structure collapses and deforms a portion of the stent. In particular, the retaining structure includes one or more pins which collapse and deform at least a portion of the stent at particular pressure points. The stent, however, substantially retains its initial length. The elongated member is coupled to a distal end of the retaining structure to enable insertion of the retaining structure with the collapsed and deformed stent into the body. This insertion enables the collapsed and deformed stent to be deployed from the retaining structure and placed into the body of the patient while maintaining substantially its initial length.

Embodiments of this aspect of the invention can include the following features. The delivery system can also include a sliding member that slides through a lumen defined by the elongated member. The sliding member exerts a deploying force on the stent to deploy the stent from the retaining structure. The delivery system can also include a handle coupled to the elongated member. The handle may also be coupled to the sliding member to allow an operator of the delivery system to use the handle to slide the sliding member through the lumen defined by the elongated member. This exerts the deploying force on the stent.

In another aspect, the invention includes a method of loading a stent into a retaining structure. The method includes providing a stent having a coil and having an initial length when in an expanded rest state. The method also includes providing a retaining structure sized for insertion into the body and having one or more pins. The method includes inserting the stent into the retaining structure so that at least a portion of the stent becomes collapsed and deformed by one or more pins while the stent retains its initial length.

The method may also include the step of providing the stent which includes a membrane coating the coil. In another embodiment, the method includes inserting the retaining structure with the collapsed and deformed stent into the body. This enables the deployment of the deformed and collapsed stent from the retaining structure and placed into the body of the patient while maintaining substantially its initial length. In a further embodiment, the method includes the step of sliding a sliding member through a lumen defined by the elongated member to deploy the collapsed and deformed stent into the body of the patient.

The directional terms proximal and distal require a point of reference. In this document, the point of reference in determining direction is from the perspective of a patient. The term "proximal" refers to a direction that points into the patient's body. The term "distal" refers to a direction that points out of the patient's body.

The foregoing and other objects, aspects, features, and advantages of the invention will become more apparent from the following description and from the claims.

BRIEF DESCRIPTION OF DRAWINGS

In the drawings, like reference characters generally refer to the same parts throughout the different views. Also, the drawings are not necessarily to scale, emphasis instead generally being placed upon illustrating the principles of the invention.

FIG. 7A is a perspective view of the proximal portion of the stent delivery system of FIG. 3A showing one pin.

FIG. 7B is another perspective view of the proximal portion of the stent delivery system of FIG. 3A showing one pin.

FIG. 7C is an end view of the stent inserted into the stent delivery system from the perspective indicated by line 7C—7C in FIG. 7A.

DESCRIPTION

Figure 1:
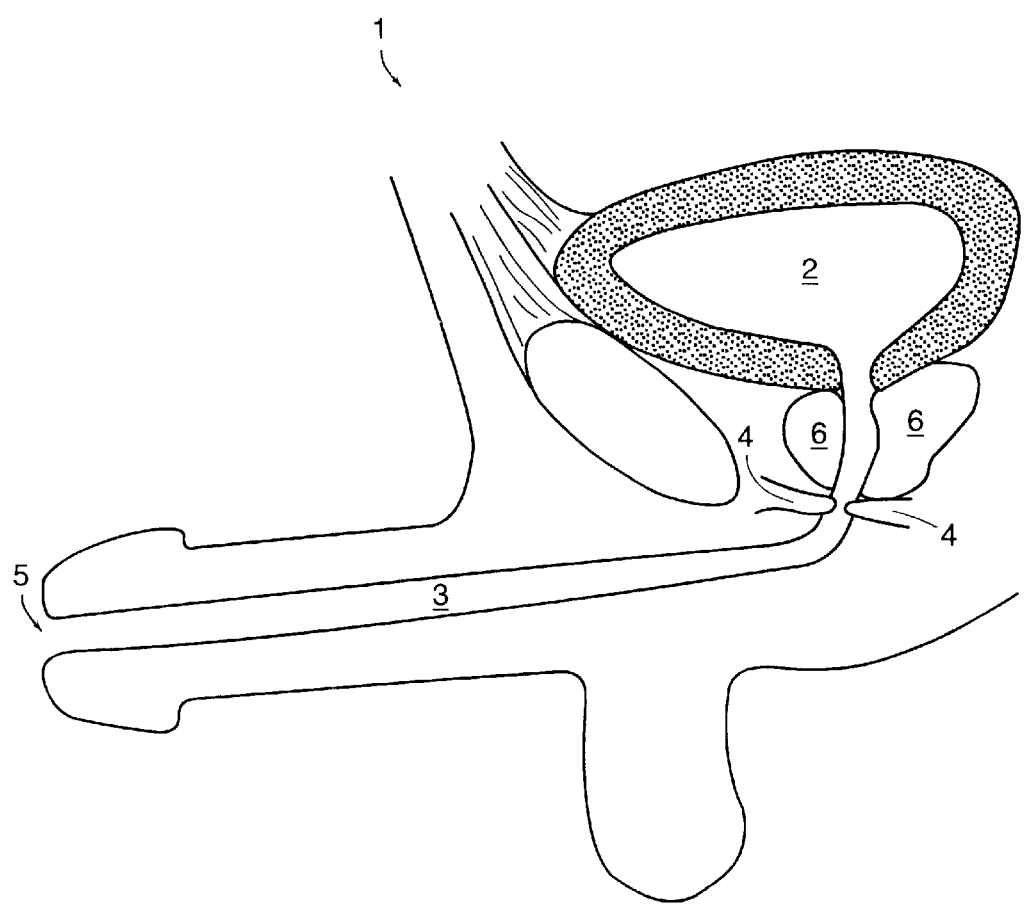
FIG. 1 is a schematic view of a male urinary system.

Urine retention and reduced urination are two common symptoms that some male patient afflicted with benign prostatic hyperplasia (BPH) endure. Benign prostatic hyperplasia is a medical condition in which a patient's prostate enlarges due to disease or a decrease in hormone production. FIG. 1 shows a male urinary system 1, which includes a bladder 2, a urethra 3, an external sphincter 4, a meatus 5, and a prostate 6. The prostate 6 is a male reproductive organ that surrounds a section of the urethra 3 generally known as the prostatic urethra. Due to the prostate's location, the male urinary system 1 may be constricted and thus obstructed when the patient's prostate 6 enlarges.

Figure 2A:
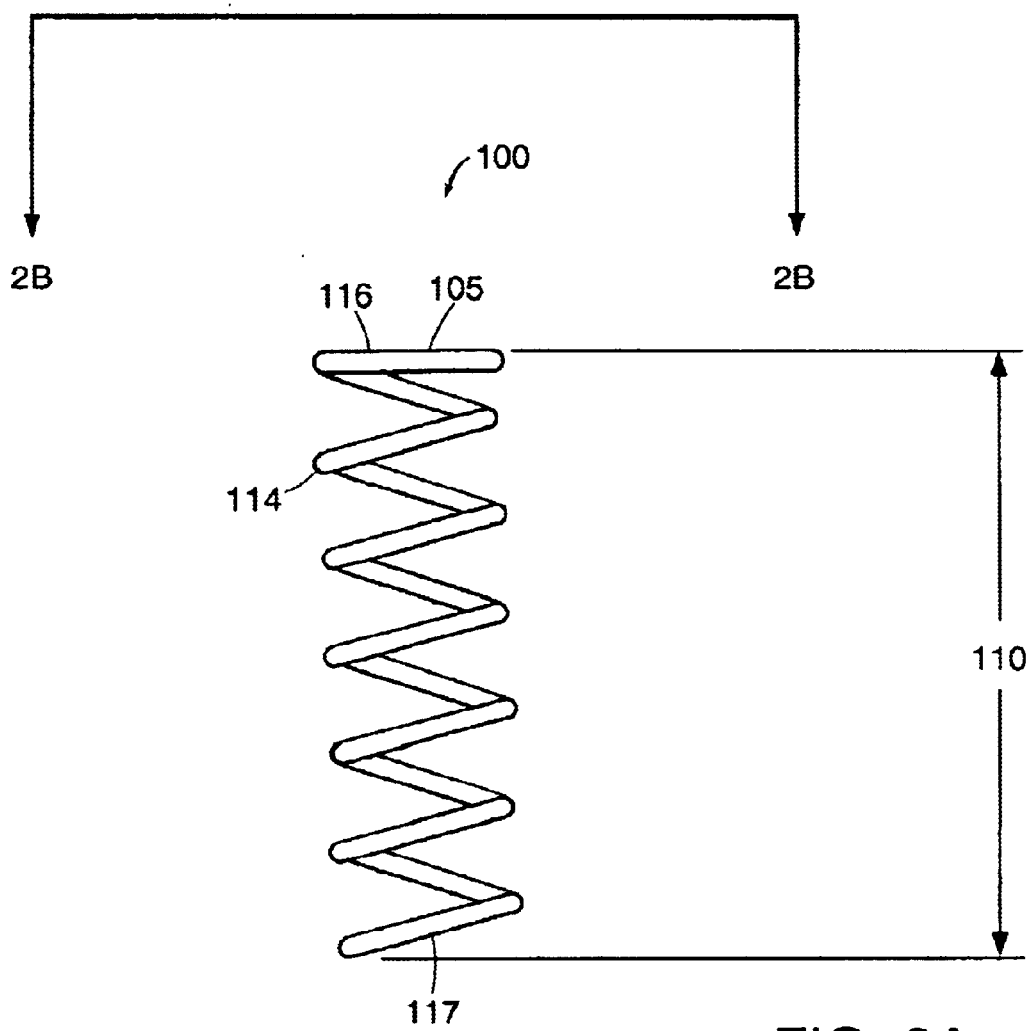
FIG. 2A is an expanded side view of one embodiment of a urethral stent of the invention.
Figure 2B:
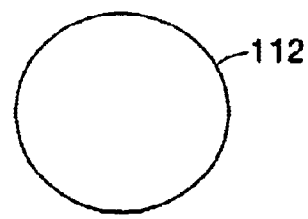
FIG. 2B is a top view of the urethral stent from the perspective indicated by line 2B—2B in FIG. 2A.
Figure 2C:
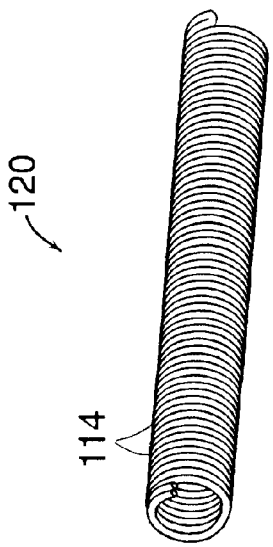
FIG. 2C is a side view of one embodiment of a single helix coil stent.
Figure 2D:
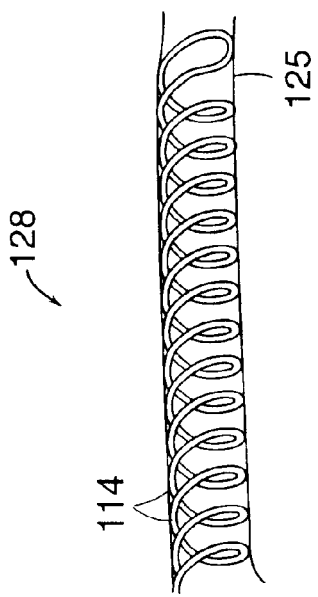
FIG. 2D is a side view of one embodiment of a double helix coil stent.

FIG. 2A illustrates an expanded side view of a urethral stent 100 to illustrate the components of the urethral stent 100. The urethral stent 100 includes a coil segment 105. The coil segment 105 defines a lumen extending within the urethral stent 100 that allows fluids, such as urine, to pass therethrough from the bladder 2 of a patient. When the urethral stent 100 is in a rest or unrestrained state in which no external or other forces are exerted upon any portion of the coil segment 105, the coil segment 105 has an initial length 110 and the lumen defined by the coil segment 105 has an initial cross-sectional area 112, as shown in FIG. 2B. The coil segment 105 has adjacent turns 114 spaced close together to prevent tissue ingrowth. The adjacent turns 114 could touch each other, or could have some small spacing between them. Whatever the spacing or positioning of the adjacent turns 114, it is sufficient to substantially prevent tissue ingrowth between adjacent turns and thus keep tissue from growing or impinging into the lumen defined by the coil segment 105 when the stent 100 is placed within the body of a patient. Although FIG. 2A illustrates significant spaces between the adjacent turns 114, FIG. 2A exaggerates the distances between the adjacent turns 114 of the urethral stent 100 for illustrative purposes only. FIGS. 2C and 2D are more accurate with respect to the spacing/closeness of the adjacent turns 114.

The coil segment 105 can be made from any biocompatible material that exhibits superelastic properties. Nickel-titanium, or nitinol, is preferable because of its superelastic or "pseudo-elastic" shape recovery properties. More specifically, these properties enable the coil segment 105 to withstand a significant amount of bending and flexing and deformation force(s), and yet return to its original and unrestrained state without becoming permanently deformed due to the force(s). Nitinol is an alloy that is characterized by its ability to be transformed from an austenitic crystal structure to a stress-induced martensitic structure at certain temperatures, and to return elastically to the austenitic shape when the stress is released. These alternating crystalline structures provide the alloy with its superelastic properties. Further, the concentration of the nickel with respect to the concentration of the titanium can be altered so long as the superelastic properties are present in the resulting coil segment 105.

The material(s) from which the coil segment 105 is made do(es) not exhibit shape memory properties. For instance, the coil segment 105 does not utilize the reversion of nitinol to its austenite form (to recover the previous shape of the coil segment 105) in response to raising the temperature of the coil segment 105. In other embodiments, the coil segment 105 is made from a biocompatible polymer, such as polyethylene (PE) or polypropylene. Whatever materials are used to form the coil segment 105, the coil segment 105 should exhibit superelastic properties in that the coil segment 105 should be able to undergo deforming force(s) and still be able to return to substantially its original, unrestrained state without any permanent deformation.

The thickness or diameter of the wire selected for the coil segment 105 influences the radial strength as well as the flexibility of the urethral stent 100. The diameter (or, more generally, the cross-sectional shape) of the wire needs to be sufficiently large to assure that proper radial strength of the urethral stent 100 is achieved. Proper radial strength is typically required to prevent occlusion of the patient's prostatic urethra from the constriction created by the patient's enlarged prostate. At the same time, however, the diameter of the wire needs to be sufficiently thin to promote winding ease and flexibility of the urethral stent 100 to accommodate the patient's anatomy. The diameter of the wire used to form the coil segment 105 is generally in the range of from about 0.1 millimeters to about 3 millimeters thick. The wire is wound to form the coil segment 105 that includes a proximal portion 116, a middle portion, and a distal portion 117. Round wire can be used, but wire with another cross-sectional shape could instead be used, such as, for example, flat or rectangular, square, elliptical, etc.

FIGS. 2C and 2D illustrate side views of two embodiments of the urethral coil stent 100 of FIG. 2A. Urethral coil stent 118 is a single-helix coil stent and urethral coil stent 120 is a double-helix coil stent. The single-helix coil stent 118 is formed by bending a wire into a coil to form the coil segment 105. The two ends of the wire in a single-helix coil stent 118 are on opposite sides of coil stent 118. The double-helix coil stent 120 includes two parts of the wire for every turn of the coil segment 105. Specifically, the double-helix coil stent 120 is formed by bending a wire into a coil and then turning one end of the wire around and tracing the coil in the reverse direction that was used to form the coil. Thus, upon completion of the double-helix coil stent 120, the two ends of the wire used to form the double-helix coil stent 120 are located on one side of the double-helix coil stent 120. Consequently, the double-helix coil stent 120 has a greater amount of support and rigidity relative to the single-helix coil stent 120 made from the same type of wire because the double-helix coil stent 120 has two portions of the wire for each turn of the coil segment 105.

As shown with urethral coil stents 118 and 120, substantially no spacing exists between adjacent turns 114 of the urethral coil stent. This prevents tissue ingrowth through the adjacent turns 114 and into the lumen defined by the urethral coil stent 118, 120, in accordance with the invention.

In another embodiment, the coil segment 105 of the urethral coil stent 100 is dipped in liquid silicone to coat the coil segment 105 with a webbing to prevent tissue ingrowth. Alternatively, the webbing, or "skin", can be made from any flexible biocompatible polymer that can stretch when the coil segment 105 is extended lengthwise, collapse when the coil segment 105 is compressed lengthwise, and flex when the coil segment 105 is bent or deformed. However the webbing is applied to the coil segment 105, the webbing could coat the exterior surface of the coil segment 105, the interior surface of the coil segment 105, or the exterior and interior surfaces of the coil segment 105. For example, if the coil segment 105 is dipped in liquid silicone, the webbing may coat the exterior and interior surfaces of the coil segment 105. Alternatively, the webbing may be applied or brushed onto the exterior surface or the interior surface of the coil segment 105.

Figure 2E:
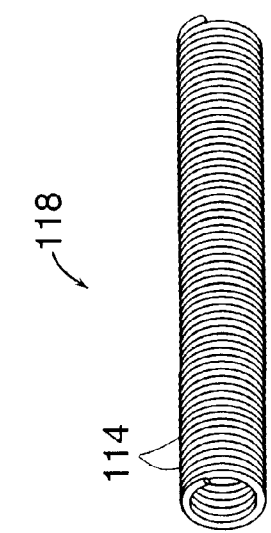
FIG. 2E is an expanded side view of another embodiment of a single helix coil stent.
Figure 2F:
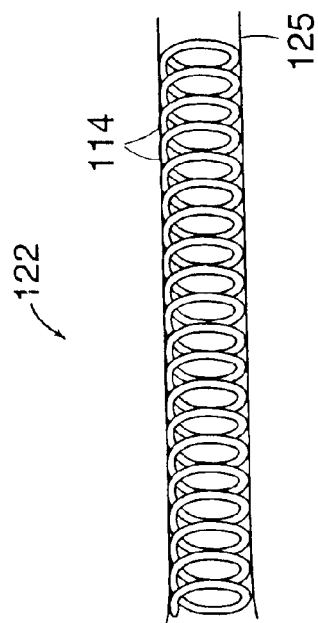
FIG. 2F is an expanded side view of another embodiment of a double helix coil stent.

FIG. 2E illustrates an expanded side view of a single-helix urethral coil stent 122 with a webbing 125 coating the exterior surface of the coil segment 105 of the urethral coil stent 122. The webbing 125 surrounds the exterior of the adjacent turns 114. The webbing 125 can be a solid, non-porous membrane that inhibits ingrowth of body tissue between the turns 114 of the coil segment 105 and prevents encrustation of the urethral coil stent 100. FIG. 2E exaggerates the distance between adjacent turns 114 of the urethral coil stent 122 to better illustrate the webbing 125 surrounding the adjacent turns 114. FIG. 2F illustrates an expanded side view of a double-helix urethral coil stent 128 with the webbing 125 surrounding the turns 114 of the double-helix coil stent 128. FIG. 2F also exaggerates the distance between adjacent turns 114 of the double-helix urethral coil stent 128 to better illustrate the webbing 125 surrounding the adjacent turns 114. Although FIGS. 2E and 2F show the webbing 125 coating the exterior of the turns 114 of the coil stent 122, 128, the webbing 125 could also coat the interior surface or the exterior and interior surfaces of the turns 114 of the coil stent 122, 128.

In one embodiment, to retain proper positioning of the urethral stent 100 within the patient's body and to inhibit movement of the positioned urethral stent 100, the middle portion of the urethral stent 100 has a smaller diameter than the proximal portion 116 and the distal portion 117 of the urethral stent 100. The middle portion, proximal portion 116, and distal portion 117 can include any number of turns 114 of the coil segments 105. The larger diameter of the distal portion 117 and the proximal portion 116 of the urethral stent 100 prevent the migration of the urethral stent 100 after insertion into the patient's urethra 3. In particular, the greater diameter of the proximal portion 116 prevents the distal migration of the urethral stent 100 (down and out of the bladder opening); whereas, the greater diameter of the distal portion 117 prevents the proximal migration of the urethral stent 100 (up into the bladder 2 of the patient).

Figure 3A:
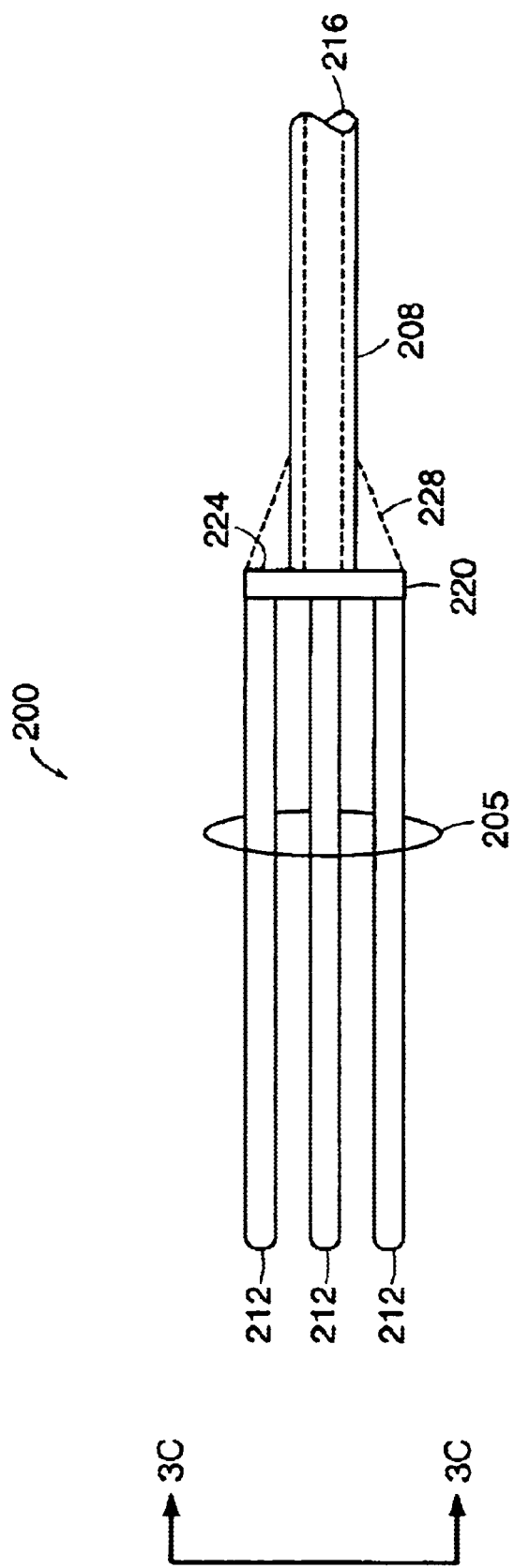
FIG. 3A is a side view of one embodiment of a distal portion of a stent delivery system according to the present invention.

Referring to FIG. 3A, an embodiment of a stent delivery system 200 according to the invention includes a retaining structure 205 and an elongated member 208. The delivery system 200 enables a urethral coil stent 100 to be collapsed and deformed upon insertion into the retaining structure 205 while the length of the collapsed and deformed urethral coil stent 100 remains the same as the initial length 110 of the urethral coil stent 100 when in its rest state. The multiple forces exerted by the retaining structure 205 on one or more portions of the urethral coil stent 100 causes the urethral coil stent 100 to maintain its initial length. Upon deployment of the urethral coil stent 100 from the stent delivery system 200, the cross-sectional area of the lumen defined by the urethral coil stent 100 expands and the length of the deployed urethral coil stent 100 remains at its initial length 110, thereby eliminating the typical shortening of a urethral coil stent upon deployment into the body of the patient. In one embodiment, the cross-sectional area of the lumen defined by the urethral coil stent 100 expands to substantially its initial cross-sectional area 112. In another embodiment, the urethral coil stent 100 does not expand to its initial cross-sectional area 112 because the urethra 3 blocks an expansion to the initial cross-sectional area 112.

In one embodiment, the retaining structure 205 includes several pins 212 to deform the urethral stent 100 upon insertion into the retaining structure 205. The pins 212 can have any size and shape so long as the pins 212 deform the urethral stent 100 so that the cross-sectional area of the lumen defined by the urethral stent 100 is reduced relative to the initial cross-sectional area 112 of the lumen defined by the urethral stent 100 when the urethral stent 100 is in its expanded rest state. As discussed in more detail below, the retaining structure 205 may have any number of pins to deform a urethral stent 100. The retaining structure 205 holds the urethral stent 100 and deforms a portion of or the entire urethral stent 100 while maintaining the initial length 110 of the urethral coil stent 100. The deformation is applied at particular pressure points, and in the disclosed embodiment along the entire length of the stent 100. More particularly, the deformation causes one portion of the urethral coil stent 100 to fold inward on the urethral stent 100. Without a physical deformation of the urethral stent 100, the urethral stent 100 would not be able to fit inside the retaining structure 205.

The elongated member 208 is coupled to the distal end of the retaining structure 205 to enable insertion of the retaining structure 205 with the collapsed and deformed urethral stent 100 while the stent 100 maintains substantially its initial length. The elongated member 208 also defines a lumen 216.

The stent delivery system 200 also includes a coupling piece 220 that couples the retaining structure 205 to the elongated member 208. In one embodiment, the lumen 216 of the elongated member 208 has a smaller cross-sectional area than the cross-sectional area of the coupling piece 220. The coupling piece 220 can have any shape (e.g., spherical, rectangular). For example, the coupling piece 220 can be rectangular to sharply transition between the elongated member 208 and the retaining structure 205. Alternatively, the coupling piece 220 can have a conical shape 228 to gradually transition between the elongated member 208 and the retaining structure 205.

Figure 3B:
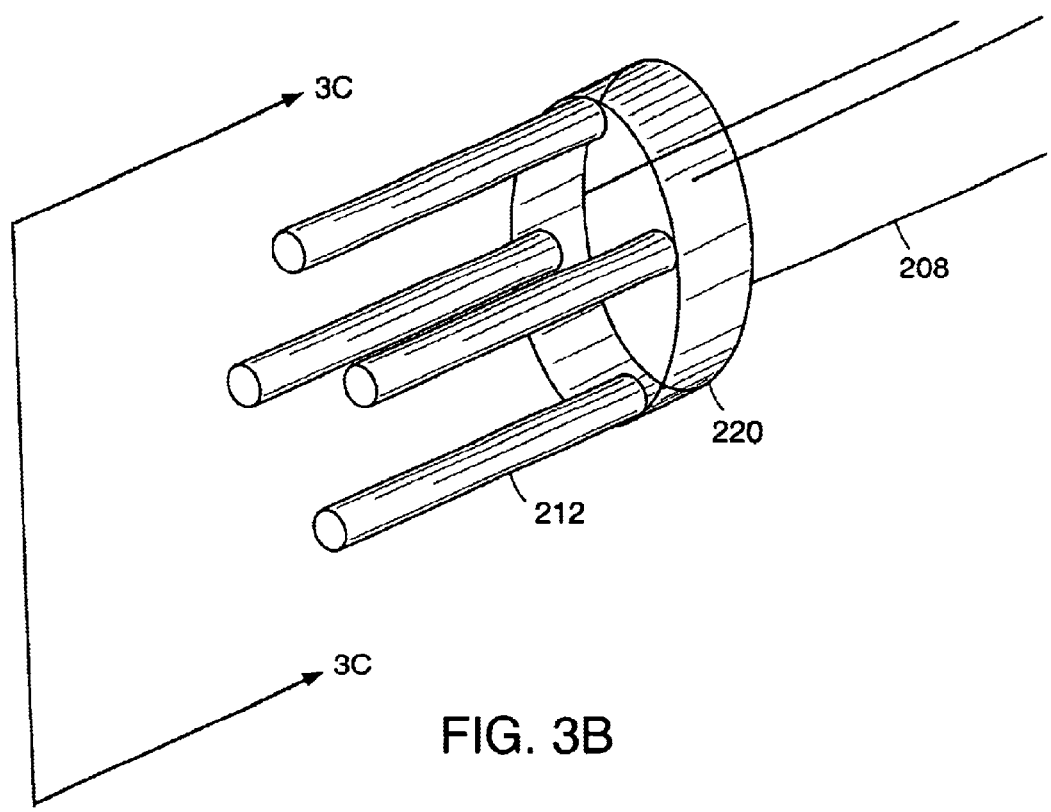
FIG. 3B is a perspective view of the proximal portion of the stent delivery system of FIG. 3A showing four pins.
Figure 3C:
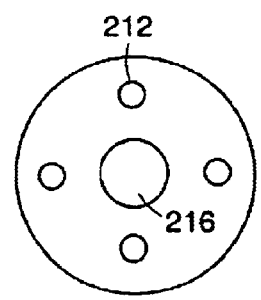
FIG. 3C is an end view of the stent delivery system from the perspective indicated by line 3C—3C in FIG. 3B and line 3C—3C in FIG. 3A.

FIG. 3B illustrates a perspective view of the proximal portion of the stent delivery system 200 of FIG. 3A showing four pins 212. The four pins 212 collapse and deform a urethral stent 100 that is inserted into the retaining structure 205. Additionally, the stent delivery system 200 shown in FIG. 3B includes a cylindrical coupling piece 220. Moreover, FIG. 3C is an end view of the stent delivery system 200 from the perspective indicated by line 3C–3C in FIG. 3B and line 3C–3C in FIG. 3A.

Figure 4A:
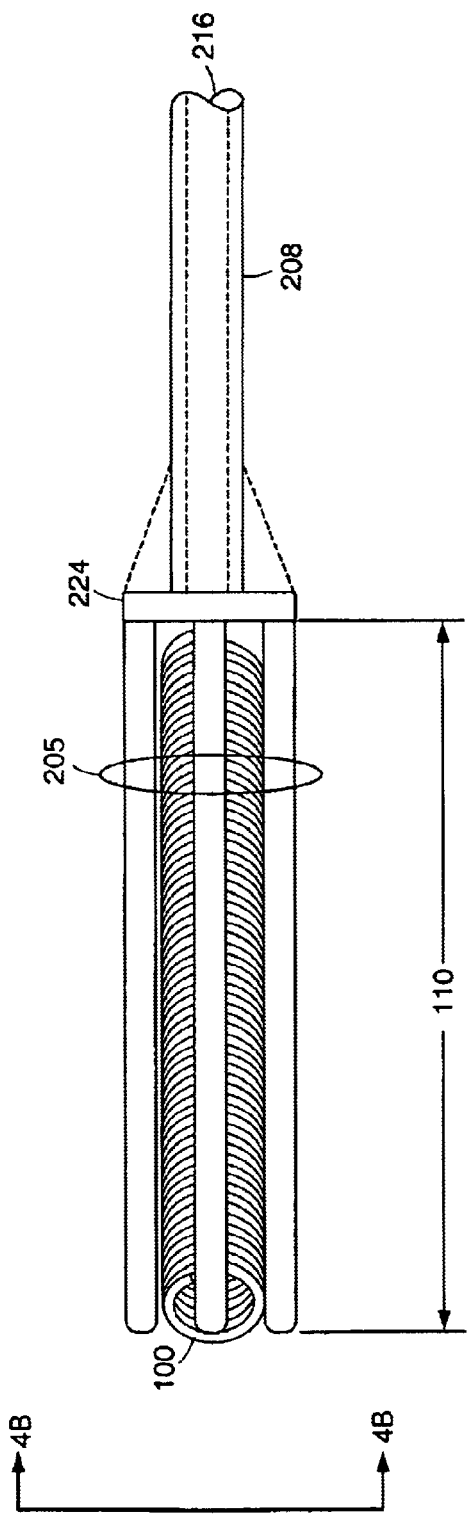
FIG. 4A is a side view of one embodiment of a urethral stent inserted into the stent delivery system shown in FIG. 3A.

Referring to FIG. 4A, the urethral stent 100 is inserted into the retaining structure 205 of the stent delivery system 200. Upon inserting the urethral stent 100 into the retaining structure 205, the four pins 212 of the retaining structure 205 collapse and deform the urethral stent 100. The cross-sectional area of the urethral stent 100 is reduced while the urethral stent 100 maintains its initial length 110. Looking along line 4B—4B of FIG. 4A, an end view of the inserted urethral stent 100 is shown in FIG. 4B. The urethral stent 100 that has been inserted into the retaining structure 205 is deformed by the four pins 212 at particular pressure points to produce four lobes 232 in the urethral stent 100.

More specifically, each pin 212 deforms the urethral stent 100 at a particular pressure point to produce a lobe 232. A pressure point can be any point on the coil segment 105. An exemplary pressure point (after the deformation of the coil segment 105) is illustrated as pressure point 230 at the bottom of the lobe 232. Thus, as shown in FIG. 4B, a pin 212 produces a lobe 232 by deforming the urethral stent 100 and, as a consequence of the deformation, two crests 231, 233 are formed. The pair of crests 231, 233 surround the lobe 232 and, more specifically, are produced as a result of the deforming force applied by a pin 212 at the particular pressure point 230. Therefore, a retaining structure 205 having four pins 212, for example, produces four lobes (e.g., lobe 232) at particular pressure points at which the pins 212 deform the urethral stent 100. Moreover, this deformation results in the production of four crests (e.g., crests 231, 233) with a crest on each side of each lobe (e.g., lobe 232).

Figure 4C:
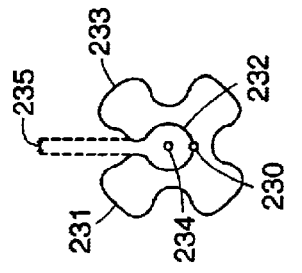
FIG. 4C is another end view of the stent inserted into the stent delivery system from the perspective indicated by line 4B—4B in FIG. 4A.
Figure 4B:
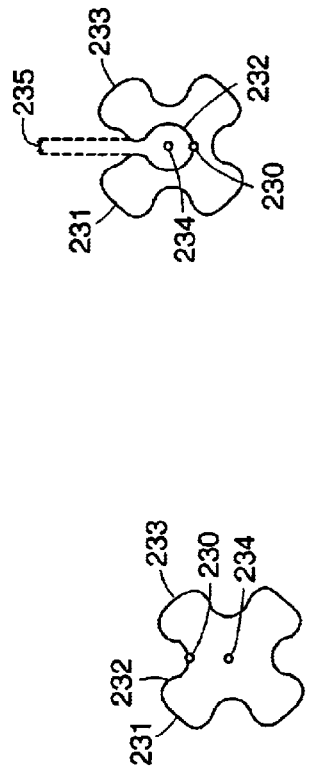
FIG. 4B is an end view of the stent inserted into the stent delivery system from the perspective indicated by line 4B—4B in FIG. 4A.

Furthermore and also referring to FIG. 4C, if a pin 212 exerts a deforming force that greatly deforms the urethral stent 100 so that the bottom of a lobe 232 extends past the center 234 of the lumen defined by the urethral stent 100 (when viewing an end view of the coil segment 105), the two surrounding crests 231, 233 exhibit greater deformation and can begin to bend towards each other. Particularly, the distance 235 between the two crests 231, 233 begins to diminish as the deformation force exerted by the pin 212 at the pressure point 230 increases. Moreover, as a pin 212 exerts a larger deformation force at the particular pressure point 230, the depth of the resulting lobe 232 also increases.

The superelastic properties of the material used to construct the coil segment 105 enable the cross-sectional area of the lumen defined by the coil segment 105 to expand to substantially its initial cross-sectional area 112 upon deployment of the urethral stent 100 (into the urethra of a patient, for example). More specifically, when the pins 212 of the retaining structure 205 lose contact with the coil segment 105, the coil segment 105 expands to substantially its initial cross-sectional area 112 in its rest state (unless the coil segment 105 is blocked by the urethra 3). During and after this expansion, however, the length of the coil segment 105 remains at the initial length 110. Thus, the deformation of the urethral coil stent 100 enables the length of the urethral coil stent 100 to maintain substantially the same length. Conversely, the length of the coil segment 105 would not remain static if the urethral coil stent 100 was wound or tightened onto the exterior of a delivering catheter.

When the coil segment 105 is released into and placed within the urethra of a patient, the surrounding urethra typically acts as a wall and a restraining force which may not allow the coil segment 105 to return fully to its rest or unrestrained state with the initial cross-sectional area 112, but in general the coil segment 105 has enough radial opening force to return substantially to its original, unrestrained form and thereby keep the urethra open.

Figure 5A:
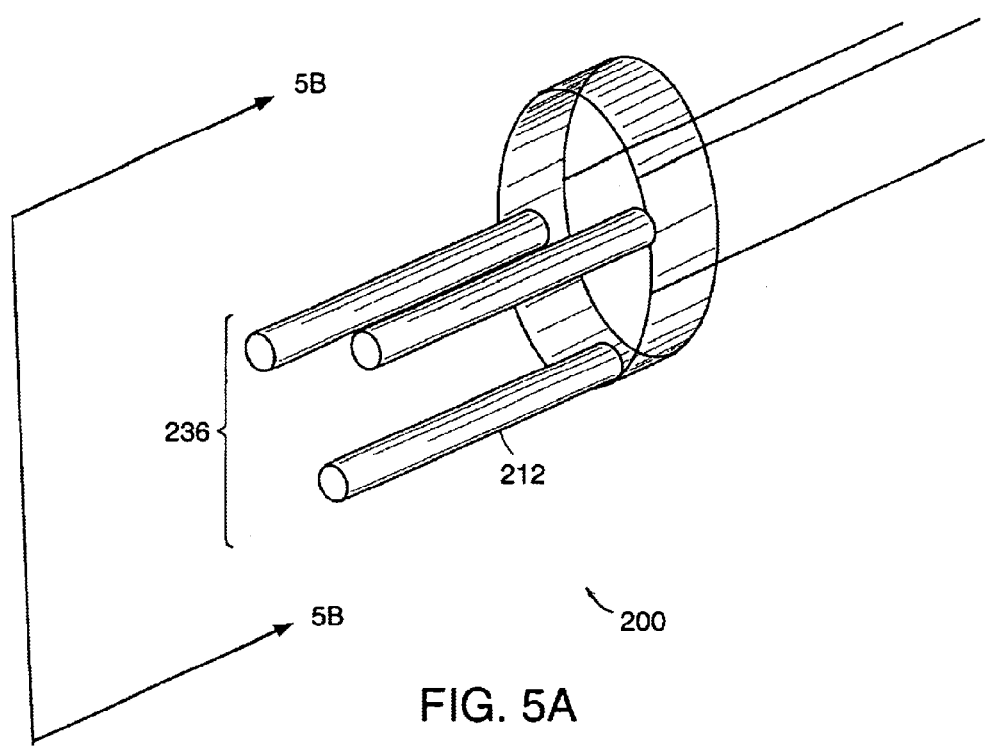
FIG. 5A is a perspective view of the proximal portion of the stent delivery system of FIG. 3A showing three pins.
Figure 5B:
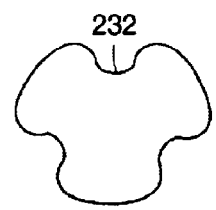
FIG. 5B is an end view of the stent inserted into the stent delivery system from the perspective indicated by line 5B—5B in FIG. 5A.

In another embodiment and referring to FIG. 5A, a retaining structure 236 of the delivery system 200 has three pins 212. FIG. 5B shows an end view of the stent inserted into the stent delivery system 200 from the perspective indicated by line 5B—5B in FIG. 5A. The three pins 212 produce a deformed urethral coil stent 100 having three lobes 232 upon insertion of the urethral stent 100 into the retaining structure 236. The pins 212 support and secure the urethral coil stent 100 while collapsing and deforming the urethral stent 100. In particular, each pin 212 of the retaining structure 236 collapses the portion of the urethral coil stent 100 that contacts the pin 212. While in the deformed state, the urethral coil stent 100 retains its initial length 110.

Figure 6A:
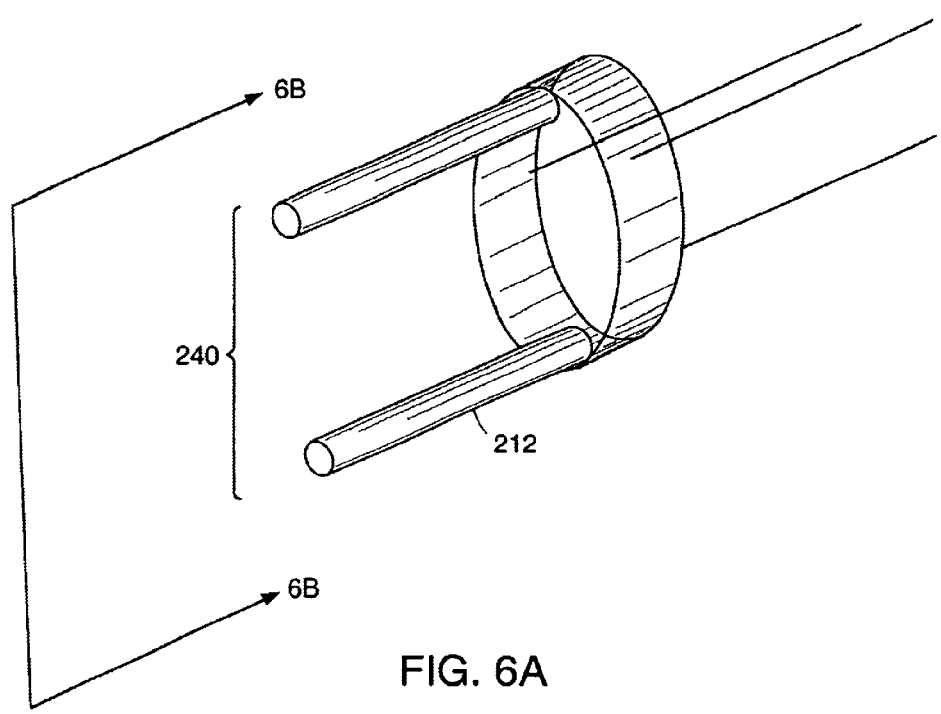
FIG. 6A is a perspective view of the proximal portion of the stent delivery system of FIG. 3A showing two pins.

Referring to FIG. 6A, a retaining structure 240 of the stent delivery system 200 has two pins 212. In one embodiment, the two pins 212 of the retaining structure 240 secure and simultaneously collapse and deform the urethral coil stent 100. The two pins 212 are parallel to each other and on the same vertical plane. The retaining structure 240 may also include a securing piece (not shown) in addition to the pins 212. As shown in more detail with respect to FIG. 7A, the securing piece would provide additional support and an additional securing device for securing the urethral coil stent 100. The securing piece would not substantially deform the urethral coil stent 100 in any manner.

Figure 6B:
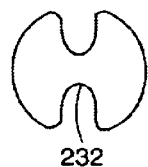
FIG. 6B is an end view of the stent inserted into the stent delivery system from the perspective indicated by line 6B—6B in FIG. 6A.
Figure 6C:
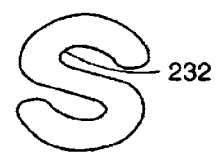
FIG. 6C is an alternative end view of the stent inserted into the stent delivery system from the perspective indicated by line 6B—6B in FIG. 6A.

FIGS. 6B and 6C show end views of the urethral coil stent 100 inserted into the stent delivery system 200 from the perspective indicated by line 6B—6B in FIG. 6A. Two lobes 232 are produced from the collapsing and deforming of the urethral coil stent 100 by the retaining structure 240 having two pins 212. The two pins 212 can alternatively have any other configuration as long as the two pins 212 can secure, collapse, and deform the urethral coil stent 100 while enabling the urethral coil stent 100 to retain its initial length 110. FIG. 6C, for example, illustrates another embodiment of an end view of the urethral coil stent 100 that is inserted into the stent delivery system 200 having a retaining structure 240 with the two pins 212 positioned in different vertical planes. Other embodiments of the retaining structure 240 having two pins 212 can be used to produce many variations on the configuration of the lobes 232 of the urethral coil stent 100.

FIG. 7A shows a perspective view of the proximal portion of the stent delivery system 200 having a retaining structure 244 with one pin 212. When having one pin 212, the retaining structure 244 has a securing piece 248 that helps secure an inserted urethral coil stent 100 without deforming the urethral coil stent 100. The securing piece 248 can be an extension of the coupling piece 220. For example, the securing piece 248 can be a cylindrical structure (as shown in FIG. 7A). Alternatively and as shown in FIG. 7B, a securing piece 250 can be an extension of a portion of the coupling piece 220, such as a curved planar structure, that provides support to and does not deform the inserted urethral coil stent 100.

Either of these examples of the retaining structure 244 having a securing piece 248 produces a urethral coil stent 100 having one lobe 212, as shown in FIG. 7C from the perspective indicated by line 7C—7C in FIG. 7A.

Figure 8:
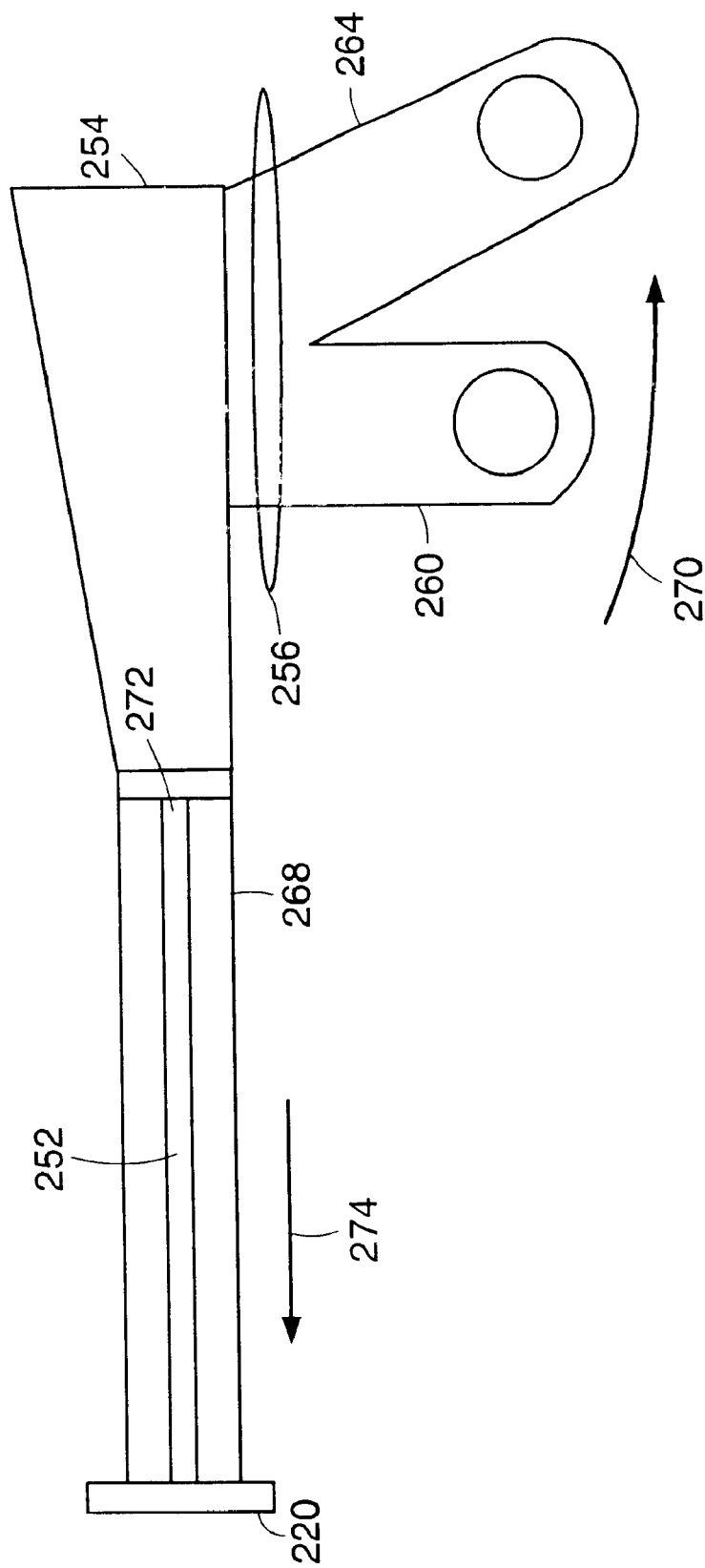
FIG. 8 is a side view of a portion of the stent delivery system of FIG. 3A.

To deploy the urethral coil stent 100 into the body of the patient, a deploying force is exerted on the distal portion 117 of the retained urethral coil stent 100 (i.e., the end closest to the coupling piece 220). The deploying force pushes the collapsed and deformed urethral coil stent 100 out of the retaining structure 205. As shown in FIG. 8, the distal portion of the stent delivery system 200 includes a sliding member 252 to exert the deploying force described above on the urethral coil stent 100 (not shown) inserted into the retaining structure 205 (not shown). The distal end 254 of the stent delivery system 200 includes a handle 256 that enables the sliding member 252 to slide along a body 268 of the stent delivery system 200. In particular, the handle 256 is coupled to the elongated member 208 and the sliding member 252. The medical professional using the stent delivery system 200 causes the handle 256 to slide the sliding member 252 through the lumen defined by the elongated member 208 to exert the deploying force on the urethral stent 100 to deploy the stent 100 from the retaining structure 205. In even more detail, the medical professional causes the sliding member 252 to slide towards the coupling piece 220 by pulling an inside handle arm 260 towards an outside handle arm 264 (shown by arrow 270).

The handle 256 may include a spring (not shown) attached from the distal end 254 of the stent delivery system 200 to the distal end 272 of the sliding member 252. The handle 256 includes the spring so that the movement of the inside handle arm 260 towards the outside handle arm 264 compresses the spring. Upon release of the handle arms 260, 264, the spring subsequently expands longitudinally to provide an actuation force on the sliding member 252. The actuation force produces movement of the sliding member 252 along line 274 so that the sliding member 252 can exert the deploying force on the urethral stent 100. Any other means can also be used to provide an actuation force on and subsequent movement of the sliding member 252.

Figure 9A:
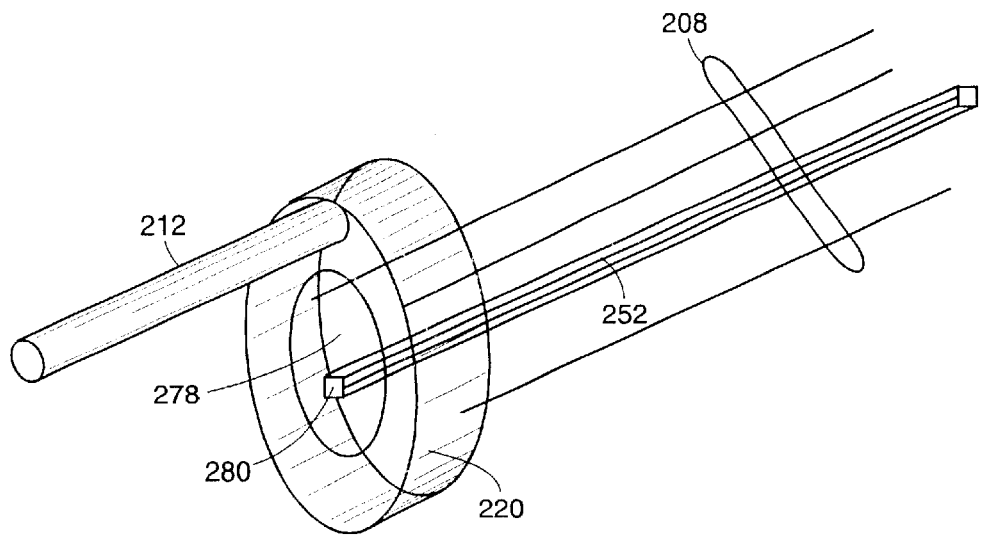
FIG. 9A is a perspective view of the proximal portion of the stent delivery system of FIG. 3A showing one pin and a sliding member.

As shown in FIG. 9A, the sliding member 252 includes a deploying mechanism 278 attached to its proximal end 280 to ensure that the sliding member 252 provides the deploying force on the urethral coil stent 100 (not shown). Without the deploying mechanism 278, the sliding member 252 may slide through the lumen defined by the urethral coil stent 100 without colliding with the urethral coil stent 100. The deploying mechanism 278 is a circular shaped member in which a portion contacts the urethral coil stent 100 as a result of the movement 274 of the sliding member 252 from the actuation force. Alternatively, the deploying mechanism 278 can be any shaped mechanism, such as a square, octagonal, and triangular, so long as the sliding member 252 provides some sort of deploying force on the urethral coil stent 100 to deploy the urethral coil stent 100 from the retaining structure 205.

Figure 9B:
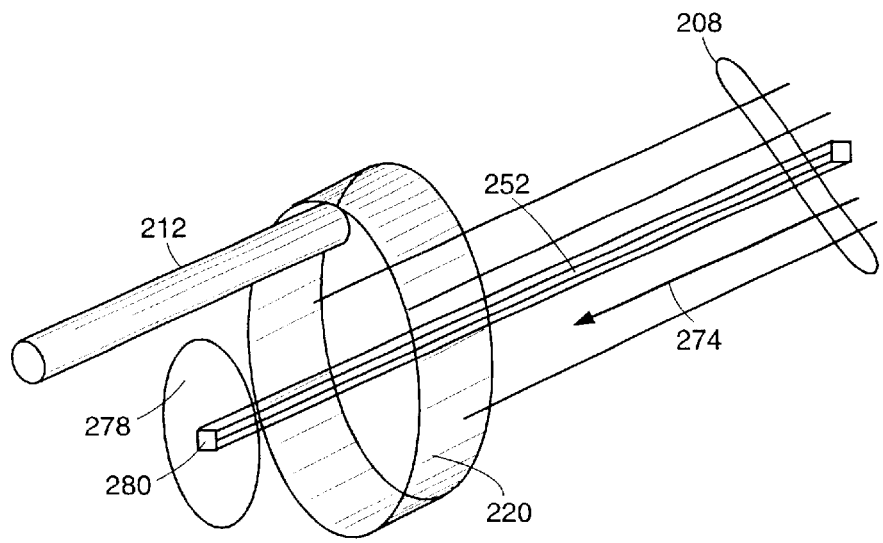
FIG. 9B is a perspective view of the proximal portion of the stent delivery system of FIG. 3A showing one pin and the sliding member of FIG. 9A extended.

Upon application of the actuation force 274 shown in FIG. 9B, the sliding member 252 slides the deploying mechanism 278 towards the distal portion 117 of the urethral coil stent 100. The sliding member 252 deploys the urethral coil stent 100 by pushing the urethral coil stent 100 out of the retaining structure 205 with the deploying mechanism 278. Although FIGS. 9A and 9B show the retaining structure 205 without a securing piece 248, 250 and with one pin 212, it is for illustrative purposes only. Additionally, the retaining structure 205 can have any number of pins with the sliding member 252 and the deploying mechanism 278.

Figure 10:
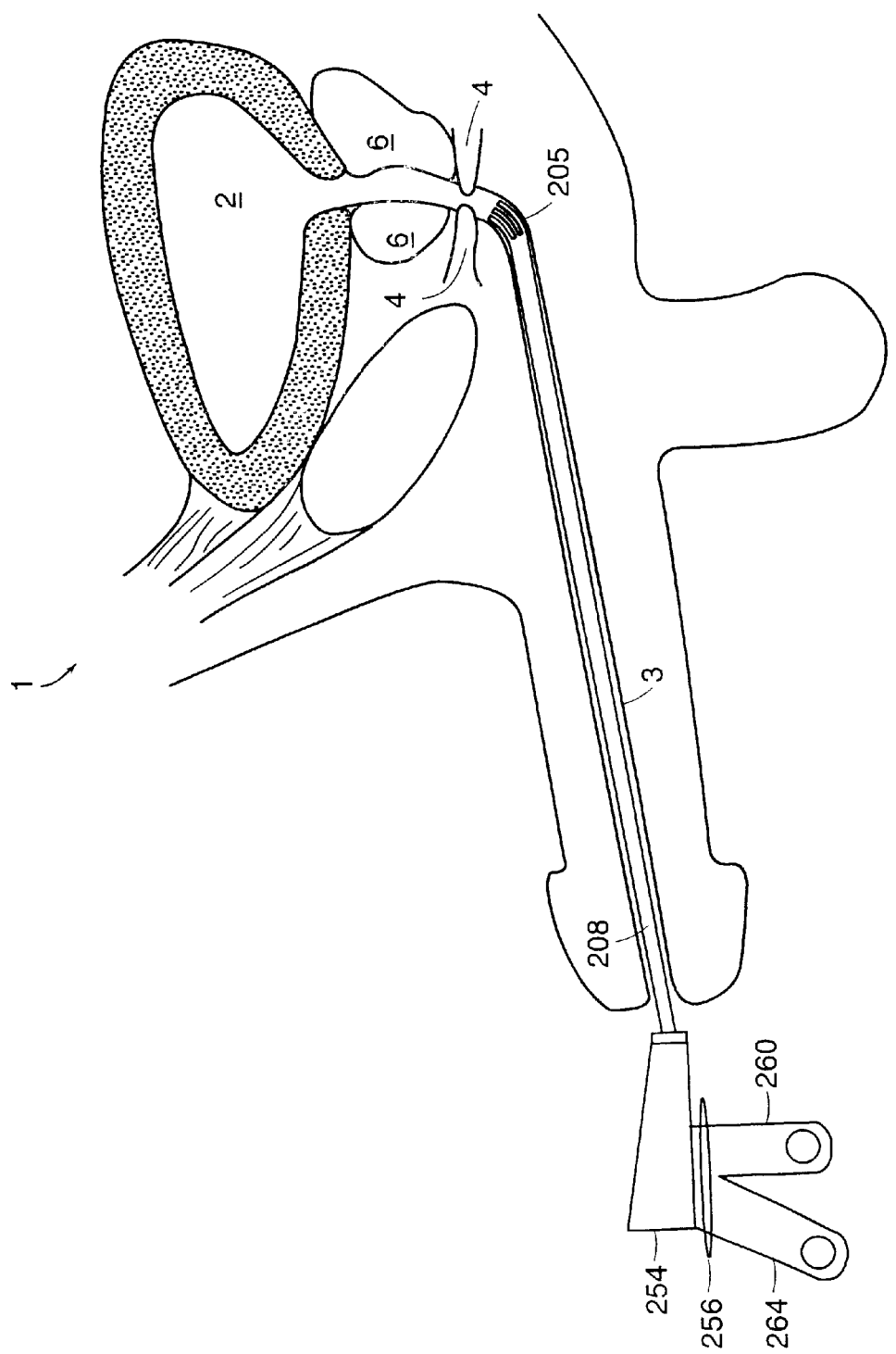
FIG. 10 is a schematic view of a stent delivery system being inserted into a male patient's urinary system.

Referring to FIG. 10, a medical professional inserts the delivery system 200 into the meatus 5 of the patient. In one embodiment, the medical professional uses the handle 256 to insert the delivery system 200 into the meatus 5. The medical professional advances the urethral stent 100 and the delivery system 200 through the patient's urinary system 1 until the urethral stent 100 is located substantially within the prostatic urethra 3 with the proximal portion 116 located near the opening of the patient's bladder 2 and the distal portion 117 terminating prior to the proximal side of the patient's external sphincter 4 so as not to interfere with the normal operation of the external sphincter 4. In particular, the elongated member 208 guides the urethral stent 100 grasped by the retaining structure 205 into the urethra 3 and into the area in which the urethra 3 is occluded by the enlarged prostate 6. In one embodiment, the retaining structure 205 and/or the elongated member 208 are flexible and one or both bend to follow the curvature of the urethra 3 as they are inserted into the body of the patient.

Figure 11:
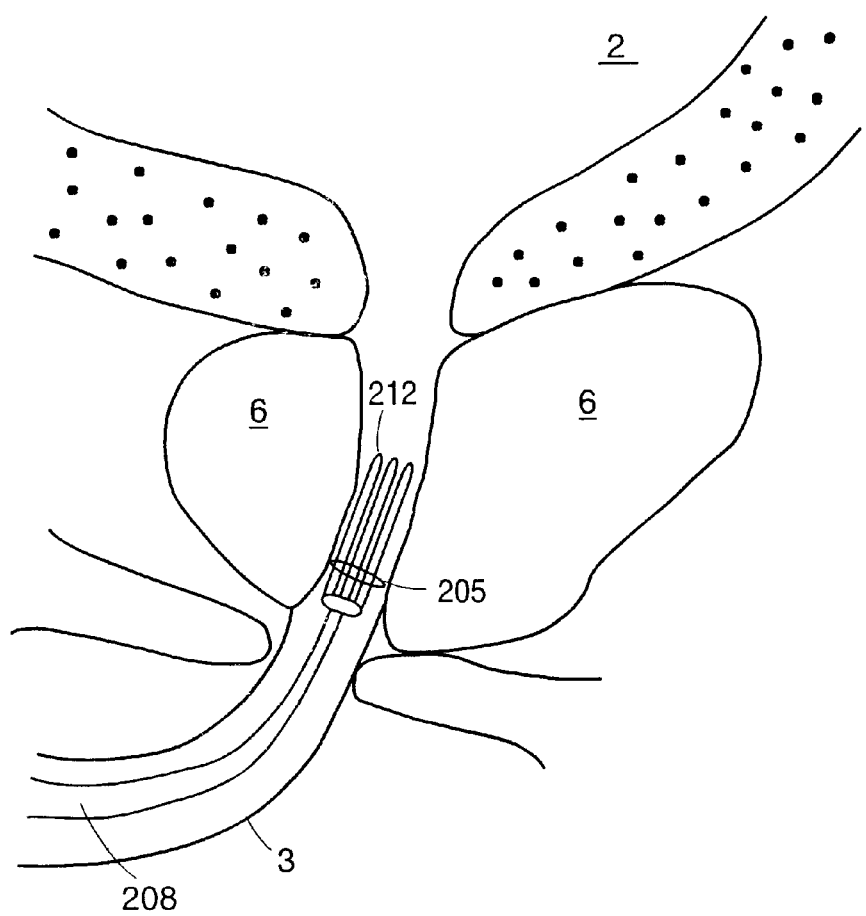
FIG. 11 is an expanded view of the stent delivery system of FIG. 10 within the male patient's urinary system.
Figure 12:
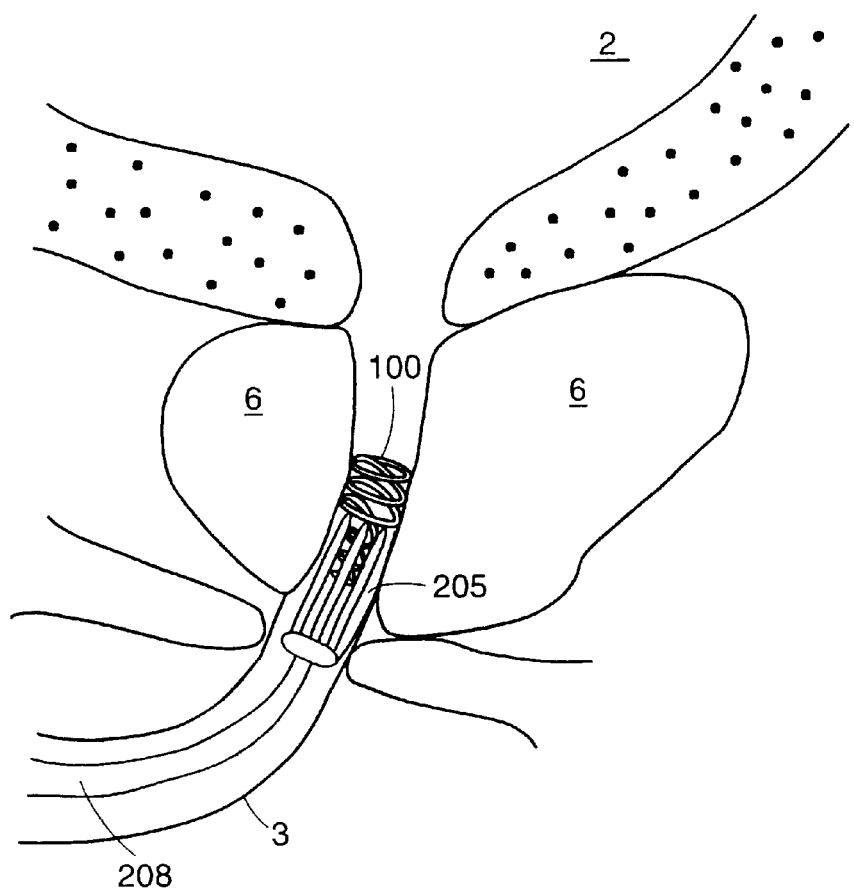
FIG. 12 is another expanded view of the stent delivery system of FIG. 10 with the stent partially deployed within the male patient's urinary system.

FIGS. 11 and 12 are expanded views of the stent delivery system 200 within the male patient's urinary system 1 as shown in FIG. 10. The retaining structure 205 holds the urethral stent 100 with the pins 212. In the embodiment shown, the urethral stent 100 is encapsulated by the webbing 125 to prevent tissue ingrowth. The medical professional inserts the stent delivery system 200 into the urethra 3 until reaching the occluded portion of the urethra 3. In one embodiment, the medical professional uses an endoscope to determine when the stent delivery system 200 reaches the occluded portion. As described previously, the urethral stent 100 maintains its initial length 110 during the insertion, positioning, and deployment of the stent delivery system 200. The medical professional then uses the handle 256 to deploy the urethral stent 100 by exerting the actuation force 274 (not shown) onto the sliding member 252, thereby deploying the urethral stent 100 by exerting the deploying force on the stent 100.

The urethral stent 100 radially expands upon deployment from the retaining structure to prop open the occluded urethra 3, while allowing the patient to control the opening and closing of his external sphincter 4 because that section of the urethra is not propped open by the stent 100. The radial expansion of the urethral stent 100 occurs without any substantial change in the length of the urethral coil stent 100, in accordance with the invention. Because the stent 100 retains its initial length 110, the medical professional can place the stent 100 with great accuracy. The stent 100 will not expand longitudinally into sections of the urethra not intended to be propped open.

At some later time, the medical professional can remove the urethral stent 100 by using a grasping device, such as forceps, to engage and remove the urethral stent 100 from the body of the patient.

Variations, modifications, and other implementations of what is described herein will occur to those of ordinary skill in the art without departing from the spirit and the scope of the invention. The invention is not to be limited only to the preceding illustrative description.

What is claimed is:

1. A delivery system for placement of a stent within a body of a patient, comprising:
   (a) a stent comprising a coil defining a lumen and having an initial length when in an expanded rest state, adjacent turns of the coil being positioned to substantially prevent tissue ingrowth through the turns and into the lumen when the stent is placed within the body;
   (b) a retaining structure sized for insertion into the body and comprising one or more pins which collapse and deform at least a portion of the stent, thereby altering the cross-sectional shape of the stent, while the stent maintains substantially its initial length; and
   (c) an elongated member coupled to a distal end of the retaining structure to enable insertion of the retaining structure with the collapsed and deformed stent into the body such that the collapsed and deformed stent can be deployed from the retaining structure and placed into the body of the patient while maintaining substantially its initial length.

2. The delivery system of claim 1 further comprising a sliding member that slides through a lumen defined by the elongated member to exert a deploying force on the stent to deploy the stent from the retaining structure.

3. The delivery system of claim 2 further comprising a handle coupled to the elongated member.

4. The delivery system of claim 3 wherein the handle is also coupled to the sliding member to allow an operator to use the handle to slide the sliding member through the lumen defined by the elongated member and thereby exert the deploying force on the stent.

5. The delivery system of claim 1 wherein the coil comprises a superelastic material.

6. The delivery system of claim 1 wherein the coil comprises a material acceptable to the body of the patient.

7. The delivery system of claim 6 wherein the material comprises an alloy of nickel-titanium or a plastic.

8. The delivery system of claim 1 wherein the stent comprises a membrane coating the coil.

9. The delivery system of claim 1 further comprising a coupling piece for coupling the elongated member to the retaining structure.

10. The delivery system of claim 9 wherein a lumen defined by the elongated member has a smaller cross-sectional area than the cross-sectional area of the coupling piece.

11. A method of loading a stent into a retaining structure, comprising:
    (a) providing a stent comprising a coil defining a lumen and having an initial length when in an expanded rest state, adjacent turns of the coil being positioned to substantially prevent tissue ingrowth through the turns and into the lumen when the stent is placed within a body of a patient;
    (b) providing a retaining structure sized for insertion into the body and comprising one or more pins; and
    (c) inserting the stent into the retaining structure such that at least a portion of the stent becomes collapsed and deformed by the one or more pins, thereby altering the cross-sectional shape of the stent, while the stent retains its initial length.

12. The method of claim 11 wherein the step of providing the stent comprises providing the stent which includes a membrane coating the coil.

13. The method of claim 11 wherein the step of providing the stent comprises providing the stent which includes a silicone coating formed by dipping the coil in liquid silicone.

14. The method of claim 11 further comprising providing an elongated member coupled to a distal end of the retaining structure.

15. The method of claim 14 further comprising inserting the retaining structure with the collapsed and deformed stent into the body such that the collapsed and deformed stent can be deployed from the retaining structure and placed into the body of the patient while maintaining substantially its initial length.

16. The method of claim 15 further comprising sliding a sliding member through a lumen defined by the elongated member.

17. The method of claim 16 further comprising exerting an actuation force on the sliding member to cause the sliding member to slide through the lumen defined by the elongated member and exert a deploying force on the stent.

18. A delivery system for placement of a stent within a body of a patient, comprising:
    (a) means for retaining at least a portion of a stent in a collapsed and deformed state with one or more pins, thereby altering the cross-sectional shape of the stent, while the collapsed and deformed stent maintains substantially an initial length, the stent having the initial length when in an expanded rest state, the stent comprising a coil defining a lumen, adjacent turns of the coil being positioned to substantially prevent tissue ingrowth through the turns and into the lumen when the stent is placed within the body; and
    (b) means, coupled to the retaining means, for enabling insertion of the retaining means with the collapsed and deformed stent into the body such that the collapsed and deformed stent can be deployed from the retaining means and placed into the body of the patient while maintaining substantially its initial length.

19. The delivery system of claim 18 further comprising means for exerting a deploying force on the stent to deploy the stent from the retaining means.

20. The delivery system of claim 18 further comprising means for coating the coil with a membrane.

* * * * *